US012275602B1

(12) United States Patent
Qu et al.

(10) Patent No.: US 12,275,602 B1
(45) Date of Patent: Apr. 15, 2025

(54) LIFTING BASKET, LIFTING BASKET GUIDING MECHANISM AND LIFTING BASKET-TYPE SAMPLE CRYOGENIC STORAGE DEVICE

(71) Applicant: SHANGHAI ORIGINCELL BIOLOGICAL CRYO EQUIPMENT CO., LTD., Shanghai (CN)

(72) Inventors: Jianguo Qu, Shanghai (CN); Yunxin Cao, Shanghai (CN)

(73) Assignee: SHANGHAI ORIGINCELL BIOLOGICAL CRYO EQUIPMENT CO., LTD., Shanghai (CN)

( * ) Notice: Subject to any disclaimer, the term of this patent is extended or adjusted under 35 U.S.C. 154(b) by 0 days.

(21) Appl. No.: 18/856,079

(22) PCT Filed: Apr. 21, 2023

(86) PCT No.: PCT/CN2023/089702
§ 371 (c)(1),
(2) Date: Oct. 11, 2024

(87) PCT Pub. No.: WO2023/221732
PCT Pub. Date: Nov. 23, 2023

(30) Foreign Application Priority Data

May 16, 2022 (CN) .......................... 202221167430.9

(51) Int. Cl.
*B65G 47/90* (2006.01)
*A01N 1/142* (2025.01)
(52) U.S. Cl.
CPC ............. *B65G 47/90* (2013.01); *A01N 1/142* (2025.01); *B65G 2201/0235* (2013.01)

(58) Field of Classification Search
CPC . B65G 47/90; B65G 2201/0235; A01N 1/142
See application file for complete search history.

(56) References Cited

U.S. PATENT DOCUMENTS 7,329,394 B2 * 2/2008 Weselak .................... B01L 1/02
435/303.1
7,395,133 B2 * 7/2008 Lowe ................... G01N 35/028
700/218

(Continued)

FOREIGN PATENT DOCUMENTS

CN        110436026 A    11/2019
CN        112189657 A    1/2021
(Continued)

*Primary Examiner* — Saul Rodriguez
*Assistant Examiner* — Ashley K Romano
(74) *Attorney, Agent, or Firm* — Bayramoglu Law Offices LLC (57) ABSTRACT

A lifting basket, a lifting basket guiding mechanism and a lifting basket-type sample cryogenic storage device are provided. The guiding mechanism includes a storage member, an auxiliary guiding member and a driving member. The storage member is placed into a liquid nitrogen tank, provided with an opening at an upper end and sleeved onto an exterior of the lifting basket for restricting removal of a cryogenic vial storage member or a cryogenic vial stored inside the lifting basket. The auxiliary guiding member is arranged above the storage member and slidably connected to the storage member, and the auxiliary guiding member is sleeved onto the exterior of the lifting basket and is in contact with the lifting basket to perform relative sliding motion through a guiding structure. The auxiliary guiding member performs vertical motion relative to a storage frame and the lifting basket under the control of the driving member.

20 Claims, 4 Drawing Sheets

(56) References Cited

U.S. PATENT DOCUMENTS

| | | | |
|---|---|---|---|
| 7,527,764 B2* | 5/2009 | Angelantoni | F25D 25/00 |
| | | | 422/561 |
| 7,861,540 B2* | 1/2011 | Cloutier | F25D 17/06 |
| | | | 62/381 |
| 8,176,747 B2* | 5/2012 | Howard | G01N 1/42 |
| | | | 62/337 |
| 9,163,869 B2* | 10/2015 | Warhurst | A01N 1/145 |
| 9,255,936 B2* | 2/2016 | Hunt | A01N 1/14 |
| 11,946,684 B2* | 4/2024 | Qu | F25D 25/027 |
| 2004/0213651 A1 | 10/2004 | Malin | |
| 2019/0291955 A1* | 9/2019 | Bastian, II | B65G 1/1373 |
| 2020/0277137 A1* | 9/2020 | Bastian, II | B66F 9/065 |
| 2021/0032034 A1* | 2/2021 | Kalouche | B25J 9/1612 |
| 2021/0300739 A1* | 9/2021 | Surjaatmadja | B66F 9/063 |
| 2022/0194248 A1* | 6/2022 | Kalouche | B65G 1/065 |

FOREIGN PATENT DOCUMENTS

| | | |
|---|---|---|
| CN | 112208942 A | 1/2021 |
| CN | 215556224 U | 1/2022 |
| CN | 215556254 U | 1/2022 |
| CN | 216187128 U | 4/2022 |
| CN | 217625232 U | 10/2022 |

\* cited by examiner

LIFTING BASKET, LIFTING BASKET GUIDING MECHANISM AND LIFTING BASKET-TYPE SAMPLE CRYOGENIC STORAGE DEVICE

CROSS REFERENCE TO THE RELATED APPLICATIONS

This application is the national phase entry of International Application No. PCT/CN2023/089702, filed on Apr. 21, 2023, which is based upon and claims priority to Chinese Patent Application No. 202221167430.9, filed on May 16, 2022, the entire contents of which are incorporated herein by reference.

TECHNICAL FIELD

The present disclosure belongs to the technical field of biological sample storage, and relates to a lifting basket, a lifting basket guiding mechanism and a lifting basket-type sample cryogenic storage device.

BACKGROUND

Long-term storage of a biological sample usually requires a lowest possible temperature to minimize biochemical reactions of the sample and improve the stability of various components of the sample. The lower the temperature, the longer the sample preservation time will be.

A cryogenic preserved sample is usually placed in a cryogenic vial to protect cells therein, the cryogenic vial is then placed in liquid nitrogen via a cryogenic rack/cryogenic box or directly submerged in the liquid nitrogen, so as to achieve long-term stable preservation of the sample. More specifically, the cryogenic rack/cryogenic box or the cryogenic vial is usually placed into a liquid nitrogen tank via a lifting basket for freezing.

At present, in order to enhance stability of the lifting basket when the lifting basket is lifted, a conventional lifting basket mechanism is provided with a plurality of sections of sliding rods or other guiding structures on sidewalls of the lifting basket, such that a scraper blade assembly on a side can easily extract a rack. However, the sliding rods and other guiding structures are not resistant to the low temperature, and will deform and frost when being immersed in the liquid nitrogen for a long period of time. Therefore, the expected stability cannot be obtained when the lifting basket is lifted, which is not conducive to the external scraper blade assembly to extract the rack and make other operations during transportation of the liquid nitrogen tank, the cryogenic rack/cryogenic box or the cryogenic vial stored inside the basket is prone to slide sideways.

SUMMARY

Objectives of the present disclosure is to provide a lifting basket, a lifting basket guiding mechanism and a lifting basket-type sample cryogenic storage device, which can solve the problem of poor stability when the lifting basket is lifted, affecting subsequent operations such as extraction, and can also solve the problem of sideways sliding of a cryogenic rack/cryogenic box or cryogenic vial stored inside the lifting basket when a liquid nitrogen tank is transported.

In order to solve the technical problem in the prior art, the present disclosure adopts a technical solution as follows:

a lifting basket guiding mechanism, including a storage member being placed into a liquid nitrogen tank as a whole, where the storage member is provided with an opening at an upper end and sleeved onto an exterior of the lifting basket and is configured to restrict the removal of a cryogenic vial storage member or a cryogenic vial stored inside the lifting basket from a side;

further including an auxiliary guiding member, where the auxiliary guiding member is arranged above the storage member and is slidably connected to the storage member, and the auxiliary guiding member is sleeved onto the exterior of the lifting basket and is in contact with the lifting basket to perform relative sliding motion through a guiding structure; and further including a driving member, where the auxiliary guiding member performs vertical motion relative to a storage frame and the lifting basket under the control of the driving member.

Optionally, the storage member includes the storage frame, where the storage frame forms a shield around sides of the lifting basket capable of restricting sideways sliding of the cryogenic vial storage member or cryogenic vial stored in the lifting basket; and the storage frame is provided with cooling ports.

Optionally, an outer side of the storage frame is further provided with a connecting member, such that the storage frame can be installed inside the liquid nitrogen tank or on a rotating mechanism inside the liquid nitrogen tank.

Optionally, the auxiliary guiding member includes an auxiliary guiding frame, one end of the auxiliary guiding frame is slidably connected to the storage frame via a slide rail and slot pair, and the other end thereof is fixedly connected to the driving member.

Optionally, the driving member includes a driving motor, an output end of the driving motor is connected to the auxiliary guiding frame via a sliding block, and the sliding block is arranged on a fixed rail.

Optionally, the guiding structure includes guiding wheels that are arranged on an inner side of the auxiliary guiding frame, and can be in contact with the lifting basket for sliding.

The above technical solution of the present disclosure has the following beneficial effects:

The storage member is sleeved onto the exterior of the lifting basket, such that the lifting basket guiding mechanism can play an excellent guiding function, and is not affected by low-temperature deformation or frosting; and when the liquid nitrogen tank is transported, it can effectively prevent the cryogenic vial storage member or the cryogenic vial stored inside the lifting basket from sliding sideways. Through the design of auxiliary guiding member and cooperation with the storage member, the guiding effects are further improved, and a positioning function is achieved, allowing precise acquisition and alignment of the cryogenic vial storage member or cryogenic vial placed inside the lifting basket, which can facilitate the lifting of the lifting basket or efficient transfer or extraction operations of the cryogenic vial storage member or cryogenic vial.

In order to solve the technical problem, the present disclosure adopts another technical solution as follows:

a lifting basket, including a lifting basket body for storing the cryogenic vial storage member or the cryogenic vial; and the lifting basket body is further provided with the lifting basket guiding mechanism.

The above technical solution of the present disclosure has the following beneficial effects:

By arranging the lifting basket guiding mechanism on the lifting basket body and leveraging the storage member and the auxiliary guiding member, an effective guiding effect of the lifting basket is realized, and the cryogenic vial storage member or the cryogenic vial stored inside the lifting basket can be prevented from sliding sideways, and precise positioning and alignment of the cryogenic vial storage member or cryogenic vial inside the lifting basket can be realized.

In order to solve the technical problem, the present disclosure adopts further another technical solution as follows:

a lifting basket-type sample cryogenic storage device, including a cryogenic storage area and an operating area, where the cryogenic storage area is provided with the liquid nitrogen tank, and the lifting basket is arranged inside the liquid nitrogen tank.

Optionally, a rotating mechanism is further arranged inside the liquid nitrogen tank, the rotating mechanism is connected to the lifting basket and is thus capable of rotating the lifting basket to a position corresponding to a storage door of the liquid nitrogen tank.

Optionally, the rotating mechanism includes a rotating motor, a rotating shaft, a supporting turntable, and a base that are connected in sequence, where the rotating motor is arranged outside the liquid nitrogen tank, the base is connected inside the liquid nitrogen tank, and the lifting basket guiding mechanism is installed on the supporting turntable.

Optionally, the operating area is provided with a lifting mechanism, which is arranged above the storage door of the liquid nitrogen tank and is configured for extracting or storing the lifting basket.

Optionally, the lifting mechanism includes a lifting motor, a slide rail, a vertical guide plate, and a lifting platform, where the lifting motor and the slide rail are fixedly connected to the vertical guide plate, and the lifting platform is slidably connected to the slide rail and is driven by the lifting motor to move up and down; and the lifting platform is provided with a hook portion for grabbing the lifting basket.

Optionally, the lifting mechanism further includes a position sensor, which is arranged on the slide rail and is configured to detect an operating position of the lifting platform.

Optionally, the driving member of the lifting basket guiding mechanism is arranged on the vertical guide plate of the lifting mechanism.

Optionally, the operating area is provided with a lid removal mechanism, which includes a lid removal motor, a lead screw nut assembly, and a lid removal plate, where the lid removal plate is arranged horizontally and fixed to nuts of the lead screw nut assembly, and an output end of the lid removal motor is coaxially connected to a lead screw of the lead screw nut assembly.

Optionally, the operating area is further provided with a scraper blade mechanism, which includes a scraper blade motor, a slide slot and slide block assembly, and a scraper blade, one end of the horizontally arranged scraper blade is fixedly connected to a slide block of the slide slot and slide block assembly, and the other end thereof is an output end of the scraper blade motor.

The above technical solution of the present disclosure has the following beneficial effects:

For the lifting basket-type sample cryogenic storage device, the lifting basket having the guiding mechanism is arranged inside the liquid nitrogen tank, more precise alignment of the cryogenic vial storage member or cryogenic vial is finally achieved, facilitating subsequent external operations such as extraction. In addition, the lifting basket can be guided to be placed into and extracted from the liquid nitrogen tank stably, and the cryogenic vial storage member or the cryogenic vial stored inside the lifting basket can be prevented from sliding sideways.

REFERENCE NUMERALS IN THE ACCOMPANYING DRAWINGS 1. cryogenic storage area; 11. liquid nitrogen tank; 11-1. valve assembly; 111. lifting basket; 1111. to-be-hung portion; 112. rotating mechanism; 1121. rotating motor; 1122. rotating shaft; 1123. supporting turntable; 1124. base; 113. lifting basket guiding mechanism; 1131. storage member; 1131-1. storage frame; 1131-2. connecting member; 1132. auxiliary guiding member; 1132-1. auxiliary guiding frame; 1132-2. slide rail and slot pair; 1132-3. guiding structure; 1133. driving member; 1133-1. driving motor; 1133-2. sliding block; and 1133-3. fixed rail; and 2. operating area; 21. lifting mechanism; 211. lifting motor; 212. slide rail; 213. vertical guide plate; 214. lifting platform; 2141. hook portion; 215. position sensor; 22. lid removal mechanism; 221. lid removal motor; 222. lead screw nut assembly; 223. lid removal plate; 23. scraper blade mechanism; 231. scraper blade motor; 232. slide slot and slide block assembly; and 233. scraper blade.

DETAILED DESCRIPTION OF THE EMBODIMENTS

The technical solution of the present disclosure will be further described below with reference to the embodiments.

With reference to FIGS. 1-4, this embodiment provides a lifting basket guiding mechanism 113, which includes a storage member 1131 being placed into a liquid nitrogen tank 11 as a whole, where the storage member 1131 is provided with an opening at an upper end and sleeved onto an exterior of the lifting basket 111, and is configured to restrict the removal of a cryogenic vial storage member or a cryogenic vial stored inside the lifting basket 111 from a side; the mechanism further includes an auxiliary guiding member 1132, where the auxiliary guiding member 1132 is arranged above the storage member 1131 and is slidably connected to the storage member, and the auxiliary guiding member 1132 is sleeved onto the exterior of the lifting basket 111 and is in contact with the lifting basket 111 to perform relative sliding motion through a guiding structure 1132-3; and the mechanism also includes a driving member 1133, where the auxiliary guiding member 1132 performs vertical motion relative to a storage frame 1131-1 and the lifting basket 111 under the control of the driving member 1133, and the cryogenic vial storage member could be a rack or an aluminum tray or other storage devices, such as a cryogenic rack or a cryogenic tray, serving as a storage device for cryogenic vials.

By arranging the auxiliary guiding member 1132, the driving member 1133 is passively driven by the auxiliary guiding member 1132 to move upwards along the lifting basket 111, and the lifting basket 111 is accordingly driven to move upwards, such that a location of the cryogenic rack or other cryogenic vial storage member or the cryogenic vial can be identified more accurately, facilitating external operations such as extracting the rack. During the process, the lifting basket 111 moves upward relative to the storage member 1131 inside the liquid nitrogen tank 11, and the storage member 1131 provides guidance for the lifting basket 111 in all directions, such that the operating stability is improved; and the storage member 1131 also shields an interior of the lifting basket 111 from a side, solving the problem that the cryogenic rack/cryogenic box, or cryogenic vial stored inside the lifting basket 111 slides sideways during the transportation of the liquid nitrogen tank 11.

In a further embodiment of the present disclosure, the storage member 1131 includes the storage frame 1131-1, where the storage frame 1131-1 forms a shield around sides of the lifting basket 111 capable of restricting sideways sliding of the cryogenic vial storage member or cryogenic vial stored in the lifting basket; and the storage frame 1131-1 is provided with cooling ports.

Figure 1:
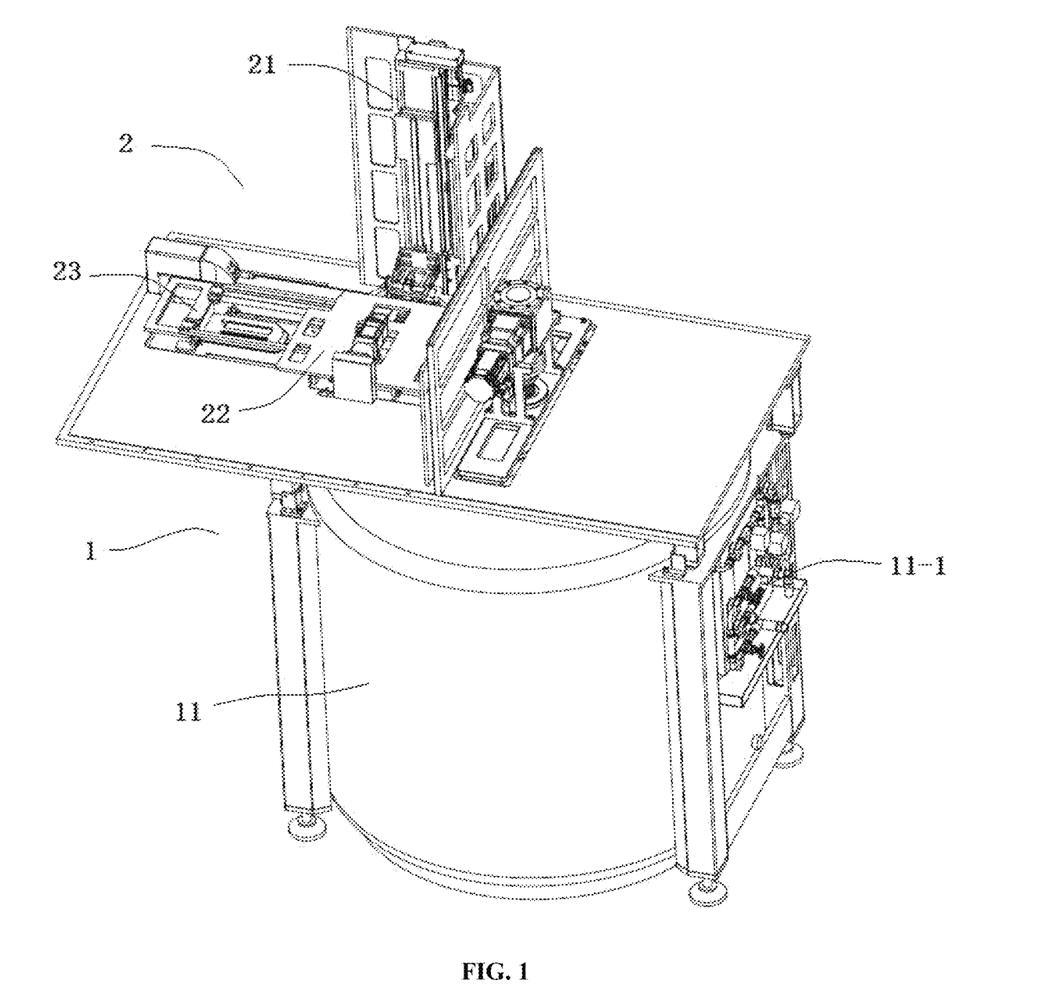
FIG. 1 is a perspective view of a lifting basket-type sample cryogenic storage device according to the present disclosure.
Figure 2:
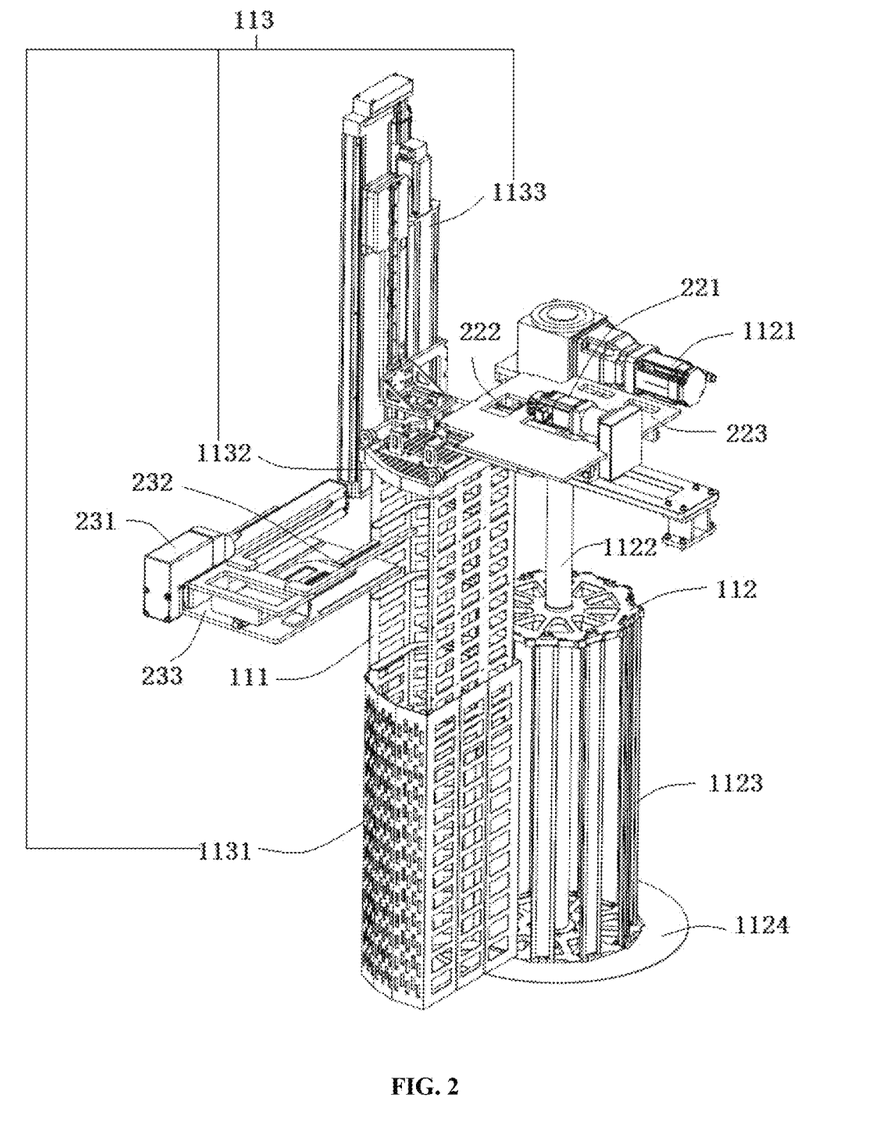
FIG. 2 is a schematic diagram of an internal structure of a lifting basket-type sample cryogenic storage device according to the present disclosure.
Figure 3:
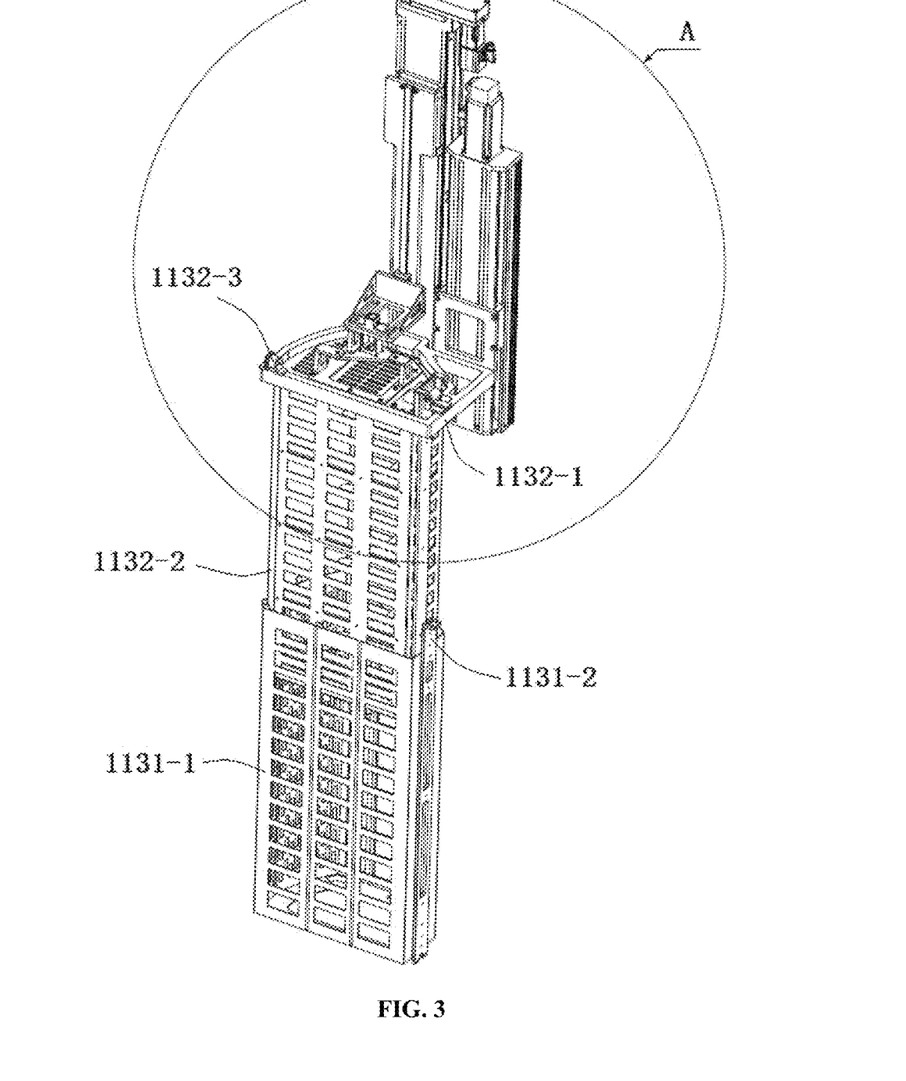
FIG. 3 is a perspective view of a lifting basket, and a lifting basket guidance mechanism, and a lifting mechanism according to the present disclosure.
Figure 4:
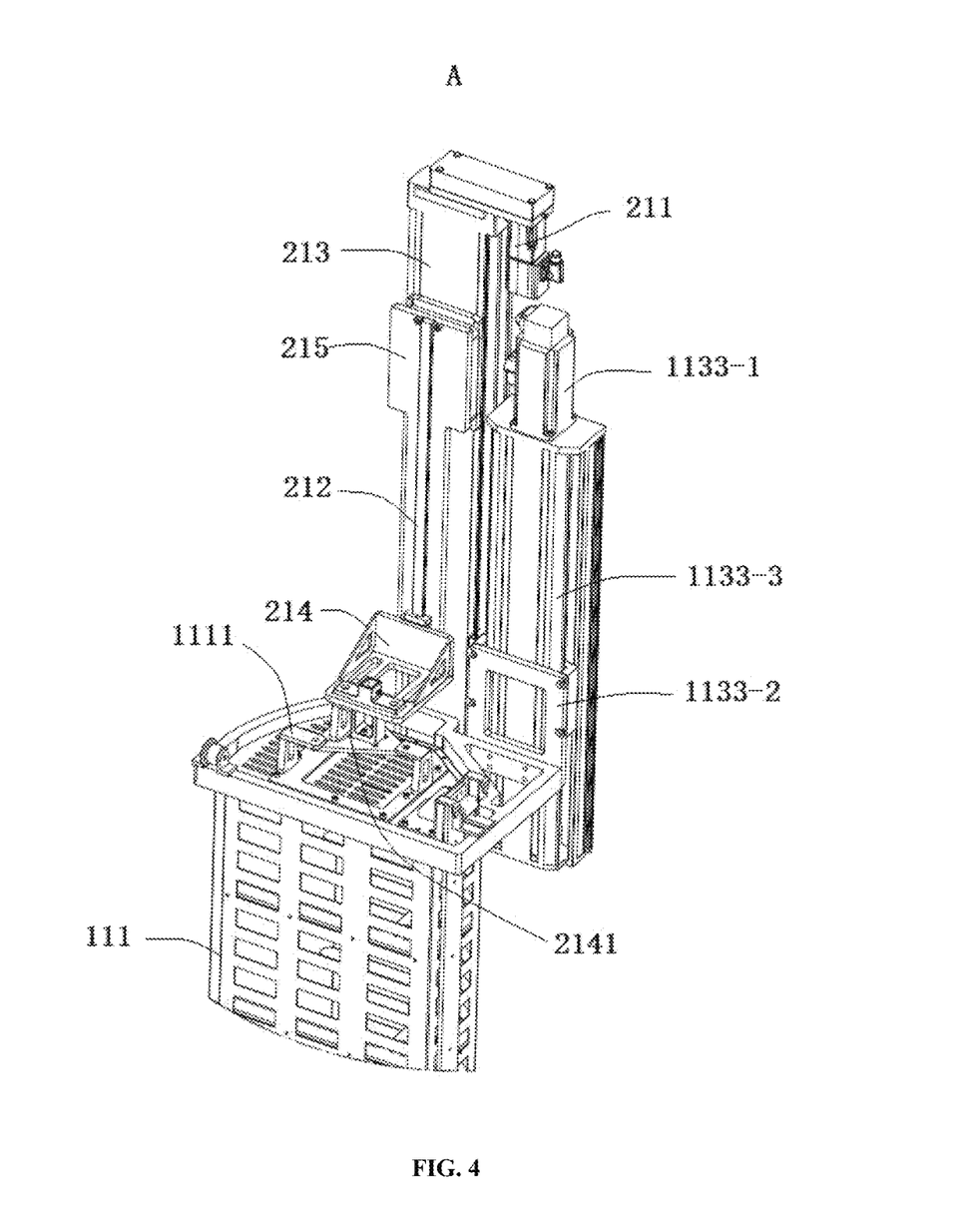
FIG. 4 is an enlarged schematic diagram in Position A in FIG. 3.

A specific structure of the storage frame 1131-1 can be a frame consistent with a shape of the lifting basket 111, as shown in FIG. 3, and a shielding structure is set around sides of the storage frame 1131-1, and the form is not limited as long as it can prevent the cryogenic vial storage member or cryogenic vial on a storage position of the lifting basket from sliding sideways. In addition, cooling ports need to be provided to improve cryopreservation effects.

In a further embodiment of the present disclosure, an outer side of the storage frame 1131-1 is further provided with a connecting member 1131-2, such that the storage frame 1131-1 can be installed inside the liquid nitrogen tank 11 or on a rotating mechanism inside the liquid nitrogen tank 11 via the connecting member 1131-2.

In a specific mode, the connecting member 1131-2 can be fixed on an outer side wall of the storage frame 1131-1, a structure of the connecting member 1131-2 can be a connecting plate extending in a length direction of a sidewall of the storage frame 1131-1, and an upper end of the connecting plate is higher than the storage frame 1131-1 and is provided with hooks. The hooks are configured to facilitate flexible assembly and disassembly, while the connecting plate is further capable of improving a structural strength of the storage frame 1131-1, and helping the storage frame 1131-1 guide and limit the lifting basket 111 from sides.

In a further embodiment of the present disclosure, the auxiliary guiding member 1132 includes an auxiliary guiding frame 1132-1, one end of the auxiliary guiding frame 1132-1 is slidably connected to the storage frame 1131-1 via a slide rail and slot pair 1132-2, and the other end thereof is fixedly connected to the driving member 1133.

The slide rail and slot pair 1132-2 includes slide rail and slide slot that are slidably matched with each other. In a specific implementation mode, the auxiliary guiding frame 1132-1 can be provided with a sliding rail on a side, and the sliding slot can be formed inside the storage frame 1131-1, or the arrangement can also be interchanged.

In a further embodiment of the present disclosure, the driving member 1133 includes a driving motor 1133-1, an output end of the driving motor 1133-1 is connected to the auxiliary guiding frame 1132-1 via a sliding block 1133-2, and the sliding block 1133-2 is arranged on a fixed rail 1133-3.

In a specific implementation mode, the sliding block 1133-2 can be set as a frame structure to enhance connection strength and reduce deadweight.

In a further embodiment of the present disclosure, the guiding structure 1132-3 includes guiding wheels that are arranged on an inner side of the auxiliary guiding frame 1132-1, and can be in contact with the lifting basket 111 for sliding. Specifically, the guiding wheels can be arranged above the auxiliary guiding frame 1132-1, such that a spatial layout is more reasonable and less likely to interfere.

This embodiment further provides a lifting basket 111, including a lifting basket body for storing the cryogenic vial storage member or the cryogenic vial; and the lifting basket body is further provided with the lifting basket guiding mechanism 113.

Since the lifting basket 111 is provided with the lifting basket guiding mechanism 113, the problems arising from entering and exiting from the liquid nitrogen tank 11, and the problems in the transportation process of the liquid nitrogen tank 11 are all solved.

This embodiment further provides a lifting basket-type sample cryogenic storage device including a cryogenic storage area 1 and an operating area 2, where the cryogenic storage area 1 is provided with the liquid nitrogen tank 11, and the lifting basket 111 is arranged inside the liquid nitrogen tank 11; the cryogenic storage area 1 and the operating area 2 can be separated by a reference plate, the reference plate is arranged above the liquid nitrogen tank 11 via a rack frame, and an area above the reference plate can be used as the operating area 2, while the area the reference plate can be used as the cryogenic storage area 1. For intelligent control, a valve assembly 11-1 can be further arranged, the valve assembly 11-1 is configured to control the nitrogen supply to the liquid nitrogen tank 11; and the valve assembly 11-1 is specifically installed on the rack frame.

Cooling and long-term storage of samples are mainly performed in the cryogenic storage area 1, the operating area 2, usually located above and outside the cryogenic storage area 1, is configured to facilitate operations such as transporting, extracting, or selecting the cryogenic vial from the cryogenic storage area. The lifting basket 111 is arranged inside the liquid nitrogen tank 11, that is, the lifting basket guiding mechanism 113 having the storage member 1131 and the auxiliary guiding member 1132 are provided, such that the lifting basket can operate stably and efficiently during both transportation and operation.

In a further embodiment of the present disclosure, a rotating mechanism 112 is further arranged inside the liquid nitrogen tank 11, the lifting basket 111 can be then connected to the rotating mechanism, and the lifting basket 111 can be then rotated to a position corresponding to a storage door of the liquid nitrogen tank. The arrangement of the rotating mechanism 112 is also conducive to uniform cooling effects of a plurality of the lifting baskets 11 inside the lifting basket 111, increasing a cooling speed.

In a further embodiment of the present disclosure, the rotating mechanism 112 includes a rotating motor 1121, a rotating shaft 1122, a supporting turntable 1123, and a base 1124 that are connected in sequence, where the rotating motor 1121 is arranged outside the liquid nitrogen tank 11, the base 1124 is connected inside the liquid nitrogen tank 11, and the lifting basket guiding mechanism 113 is installed on the supporting turntable 1123.

In a further embodiment of the present disclosure, the operating area 2 is provided with a lifting mechanism 21, which is arranged above the storage door of the liquid nitrogen tank 11 and is configured for extracting or storing the lifting basket 111. After being connected to the lifting basket 111, the lifting mechanism 21 is capable of moving upwards to extract the lifting basket 111 from the liquid nitrogen tank 11, or capable of moving downwards to place the lifting basket 111 into the liquid nitrogen tank 11.

In a further embodiment of the present disclosure, the lifting mechanism 21 includes a lifting motor 211, a slide rail 212, a vertical guide plate 213, and a lifting platform 214, where the lifting motor 211 and the slide rail 212 are fixedly connected to the vertical guide plate 213, and the lifting platform 214 is slidably connected to the slide rail 212 and is driven by the lifting motor 211 to move up and down; and the lifting platform 214 is provided with a hook portion 2141 for grabbing the lifting basket 111.

In a specific implementation mode, the lifting platform 214 can be designed as a right-angle bracket, such that the hook portion 2141 that is capable of being connected to the slide rail 212 in a vertical direction can be arranged below the lifting platform. A shape of the hook portion 2141 can be designed in a way of being matched with a to-be-hung portion 1111 of the lifting basket 111, for example, when the to-be-hung portion 1111 is a pair of inverted L-shaped elements, the hook portion 2141 can be composed of a vertical rod connected to a triangular plate, such that three tips of the triangular plate can be used to simultaneously grip the two L-shaped elements from various directions.

In a further embodiment of the present disclosure, the lifting mechanism 21 further includes a position sensor 215, which is arranged on the slide rail 212 and is configured to detect an operating position of the lifting platform 214; specifically, the position sensor 215 can be arranged at an upper end of a travel range of the slide rail 212; when sliding to a position of the position sensor, the lifting platform 214 will not continue to move upwards any longer, or it means that the lifting basket 111 has risen to a predetermined position, for example, it has been completely moved out from the storage frame 1131-1, a corresponding prompt signal will be given to facilitate other operations.

In a further embodiment of the present disclosure, the driving member 1133 of the lifting basket guiding mechanism 113 is arranged on the vertical guide plate 213 of the lifting mechanism 21. Since the auxiliary guiding member 1132 is sleeved on the lifting basket 111, their respective vertical motion structures are also centrally arranged accordingly, which is conducive to making structural layout more reasonable.

In a further embodiment of the present disclosure, the operating area 2 is provided with a lid removal mechanism 22, which includes a lid removal motor 221, a lead screw nut assembly 222, and a lid removal plate 223, where the lid removal plate 223 is arranged horizontally and fixed to nuts of the lead screw nut assembly 222, and an output end of the lid removal motor 221 is coaxially connected to a lead screw of the lead screw nut assembly 222. Through the lid removal mechanism 22, a lid body of the liquid nitrogen tank 11 or a temporary storage tank can be opened or closed.

In a further embodiment of the present disclosure, the operating area 2 is further provided with a scraper blade mechanism 23, which includes a scraper blade motor 231, a slide slot and slide block assembly 232, and a scraper blade 233, one end of the horizontally arranged scraper blade 233 is fixedly connected to a slide block of the slide slot and slide block assembly 232, and the other end thereof is an output end of the scraper blade motor 231. Through the scraper blade mechanism 23, the cryogenic rack or cryogenic box and cryogenic vial storage member can be stored into or extracted from the lifting basket.

Finally, it should be noted that the above embodiments are merely intended to illustrate the technical solution of the present disclosure, but not to limit the same; although the present invention has been described in detail with reference to the foregoing embodiments, it should be understood by those of ordinary skill in the art that the technical solutions described in the foregoing embodiments may be modified or equivalents may be substituted for some of the technical features thereof; and the modification or substitution does not make the essence of the corresponding technical solution deviate from the spirit and the scope of the technical solution of each embodiment of the present disclosure.

What is claimed is:

1. A lifting basket guiding mechanism, comprising a storage member being placed into a liquid nitrogen tank as a whole, wherein the storage member is provided with an opening at an upper end and sleeved onto an exterior of a lifting basket and is configured to restrict a removal of a cryogenic vial storage member or a cryogenic vial stored inside the lifting basket from a side;

further comprising an auxiliary guiding member, wherein the auxiliary guiding member is arranged above the storage member and is slidably connected to the storage member, and the auxiliary guiding member is sleeved onto the exterior of the lifting basket and is in contact with the lifting basket to perform relative sliding motion through a guiding structure; and further comprising a driving member, wherein the auxiliary guiding member performs vertical motion relative to a storage frame and the lifting basket under a control of the driving member.

2. The lifting basket guiding mechanism according to claim 1, wherein the storage member comprises the storage frame, wherein the storage frame forms a shield around sides of the lifting basket capable of restricting sideways sliding of the cryogenic vial storage member or the cryogenic vial stored in the lifting basket; and the storage frame is provided with cooling ports.

3. The lifting basket guiding mechanism according to claim 2, wherein an outer side of the storage frame is further provided with a connecting member, such that the storage frame can be installed inside the liquid nitrogen tank or on a rotating mechanism inside the liquid nitrogen tank.

4. The lifting basket guiding mechanism according to claim 3, wherein the auxiliary guiding member comprises an auxiliary guiding frame, one end of the auxiliary guiding frame is slidably connected to the storage frame via a slide rail and slot pair, and the other end thereof is fixedly connected to the driving member.

5. The lifting basket guiding mechanism according to claim 4, wherein the driving member comprises a driving motor, an output end of the driving motor is connected to the auxiliary guiding frame via a sliding block, and the sliding block is arranged on a fixed rail.

6. The lifting basket guiding mechanism according to claim 4, wherein the guiding structure comprises guiding wheels that are arranged on an inner side of the auxiliary guiding frame, and can be in contact with the lifting basket for sliding.

7. A lifting basket, comprising a lifting basket body for storing the cryogenic vial storage member or the cryogenic vial; and the lifting basket body is further provided with the lifting basket guiding mechanism according to claim 1.

8. A lifting basket-type sample cryogenic storage device, comprising a cryogenic storage area and an operating area, wherein the cryogenic storage area is provided with a liquid nitrogen tank, and the lifting basket according to claim 7 is arranged inside the liquid nitrogen tank.

9. The lifting basket-type sample cryogenic storage device according to claim 8, wherein a rotating mechanism is further arranged inside the liquid nitrogen tank, the rotating mechanism is connected to the lifting basket and is thus capable of rotating the lifting basket to a position corresponding to a storage door of the liquid nitrogen tank.

10. The lifting basket-type sample cryogenic storage device according to claim 9, wherein the rotating mechanism comprises a rotating motor, a rotating shaft, a supporting turntable, and a base that are connected in sequence, wherein the rotating motor is arranged outside the liquid nitrogen tank, the base is connected inside the liquid nitrogen tank, and the lifting basket guiding mechanism is installed on the supporting turntable.

11. The lifting basket-type sample cryogenic storage device according to claim 8, wherein the operating area is provided with a lifting mechanism, which is arranged above a storage door of the liquid nitrogen tank and is configured for extracting or storing the lifting basket.

12. The lifting basket-type sample cryogenic storage device according to claim 11, wherein the lifting mechanism comprises a lifting motor, a slide rail, a vertical guide plate, and a lifting platform, wherein the lifting motor and the slide rail are fixedly connected to the vertical guide plate, and the lifting platform is slidably connected to the slide rail and is driven by the lifting motor to move up and down; and the lifting platform is provided with a hook portion for grabbing the lifting basket.

13. The lifting basket-type sample cryogenic storage device according to claim 12, wherein the lifting mechanism further comprises a position sensor, which is arranged on the slide rail and is configured to detect an operating position of the lifting platform.

14. The lifting basket-type sample cryogenic storage device according to claim 11, wherein the driving member of the lifting basket guiding mechanism is arranged on the vertical guide plate of the lifting mechanism.

15. The lifting basket-type sample cryogenic storage device according to claim 8, wherein the operating area is provided with a lid removal mechanism, which comprises a lid removal motor, a lead screw nut assembly, and a lid removal plate, wherein the lid removal plate is arranged horizontally and fixed to nuts of the lead screw nut assembly, and an output end of the lid removal motor is coaxially connected to a lead screw of the lead screw nut assembly.

16. The lifting basket-type sample cryogenic storage device according to claim 8, wherein the operating area is further provided with a scraper blade mechanism, which comprises a scraper blade motor, a slide slot and slide block assembly, and a scraper blade, one end of the horizontally arranged scraper blade is fixedly connected to a slide block of the slide slot and slide block assembly, and the other end thereof is an output end of the scraper blade motor.

17. The lifting basket according to claim 7, wherein in the lifting basket guiding mechanism, the storage member comprises the storage frame, wherein the storage frame forms a shield around sides of the lifting basket capable of restricting sideways sliding of the cryogenic vial storage member or the cryogenic vial stored in the lifting basket; and the storage frame is provided with cooling ports.

18. The lifting basket according to claim 17, wherein in the lifting basket guiding mechanism, an outer side of the storage frame is further provided with a connecting member, such that the storage frame can be installed inside the liquid nitrogen tank or on a rotating mechanism inside the liquid nitrogen tank.

19. The lifting basket according to claim 18, wherein in the lifting basket guiding mechanism, the auxiliary guiding member comprises an auxiliary guiding frame, one end of the auxiliary guiding frame is slidably connected to the storage frame via a slide rail and slot pair, and the other end thereof is fixedly connected to the driving member.

20. The lifting basket according to claim 19, wherein in the lifting basket guiding mechanism, the driving member comprises a driving motor, an output end of the driving motor is connected to the auxiliary guiding frame via a sliding block, and the sliding block is arranged on a fixed rail.

* * * * *